United States Patent
Kim et al.

(10) Patent No.: US 12,125,497 B2
(45) Date of Patent: Oct. 22, 2024

(54) PAIRED NEURAL NETWORKS FOR DIAGNOSING HEALTH CONDITIONS VIA SPEECH

(71) Applicant: Canary Speech, LLC, Spanish Fork, UT (US)

(72) Inventors: Samuel Kim, La Palma, CA (US); Namhee Kwon, Redondo Beach, CA (US); Nathan Blaylock, San Antonio, TX (US); Henry J. O'Connell, Spanish Fork, UT (US); Jeffrey P. Adams, Tyngsborough, MA (US)

(73) Assignee: CANARY SPEECH, LLC, Spanish Fork, UT (US)

( * ) Notice: Subject to any disclaimer, the term of this patent is extended or adjusted under 35 U.S.C. 154(b) by 196 days.

(21) Appl. No.: 17/468,288

(22) Filed: Sep. 7, 2021

(65) Prior Publication Data
US 2023/0072242 A1 Mar. 9, 2023

(51) Int. Cl.
*G10L 25/06* (2013.01)
*G10L 15/05* (2013.01)
*G10L 15/16* (2006.01)
*G10L 25/66* (2013.01)

(52) U.S. Cl.
CPC .............. *G10L 25/66* (2013.01); *G10L 15/05* (2013.01); *G10L 15/16* (2013.01)

(58) Field of Classification Search
None
See application file for complete search history.

(56) References Cited

U.S. PATENT DOCUMENTS

| | | | |
|---|---|---|---|
| 2017/0084295 A1* | 3/2017 | Tsiartas | G10L 17/08 |
| 2020/0075040 A1* | 3/2020 | Provost | G06N 3/044 |
| 2023/0329630 A1* | 10/2023 | Patel | G16H 40/20 |

FOREIGN PATENT DOCUMENTS

WO 2021081418 A1 4/2021

OTHER PUBLICATIONS

L. Sun, et al., "Multimodal Cross- and Self-Attention Network for Speech Emotion Recognition," ICASSP 2021, Jun. 2021, pp. 4275-4279 (Year: 2021).*

(Continued)

*Primary Examiner* — Nicole A K Schmieder
(74) *Attorney, Agent, or Firm* — Kunzler Bean & Adamons

(57) ABSTRACT

A health condition or change in health condition of a person may be determined by processing the person's speech with a neural network. Speech from more than one time period may be processed and, in some implementations, speech from a time period may be associated with a health condition label. For each time period, a feature vector may be computed from the speech and the feature vector may be processed with a neural network to obtain a speech embedding vector. In some implementations, feature vector may include word-piece encodings and the neural network may be a transformer neural network. The speech embedding vectors may be processed with a mathematical model to determine a change in a health condition between two time periods or to determine a health condition label for a specific time period. In some implementations, the mathematical model may be a regression model or a fully-connected neural network.

19 Claims, 7 Drawing Sheets

(56) References Cited

OTHER PUBLICATIONS

Q. Li, et al., "Hierarchical Transformer Network for Utterance-Level Emotion Recognition," Appl. Sci. 2020, 10, 4447 (Year: 2020).*

Acheampong, et al., "Transformer models for text-based emotion detection: a review of BERT-based approaches," Artificial Intelligence Review, Feb. 2021, 54:5789-5829 (Year: 2021).*

Pappagari, et al., "Using state of the art speaker recognition and natural language processing technologies to detect Alzheimer's disease and assess its severity," ISCA, 2020 (Year: 2020).*

European Patent Application No. 22194459.8, European Search Report, Feb. 1, 2023.

* cited by examiner

PAIRED NEURAL NETWORKS FOR DIAGNOSING HEALTH CONDITIONS VIA SPEECH

BACKGROUND

Improved diagnosis of health conditions has numerous advantages for society. For example, improved diagnosis of health conditions may improve quality of life, increase life expectancy, and even lower medical costs where earlier diagnosis and treatment may be more effective than later diagnosis and treatment.

Health conditions may be diagnosed in a variety of ways. Some health conditions may be diagnosed using the speech of a patient. For example, the speech of a person may be used in diagnosing mental health conditions (stress, depression, anxiety), concussions, Alzheimer's disease, and congestive heart failure.

In some instances, a person may listen to a person's speech and use qualities of the speech in determining a diagnosis. In some instances, mathematical models (such as neural networks) may process speech to determine a diagnosis and may provide a more accurate diagnosis than a trained medical professional. Improved techniques for diagnosing health conditions with mathematical models may provide numerous additional advantages for society.

BRIEF DESCRIPTION OF THE FIGURES

The invention and the following detailed description of certain embodiments thereof may be understood by reference to the following figures.

DETAILED DESCRIPTION

The voices of different people sound different and have various different qualities and aspects to them. The different sounds of different people's voices may make it more difficult to diagnose a health condition. For a simple example, for a first person, his or her voice may normally sound smooth, but that person's voice may become hoarse after speaking for an extended period of time where they have "lost their voice." For a second person, however, his or her voice may always sound hoarse and that may be their normal manner of speaking.

To improve the diagnosis of health conditions via processing of a person's voice, samples of the person's voice from multiple time periods may be used. Continuing with the example above, a sample of a person's voice from a first time period when the person is not hoarse will be helpful in determining, at a second time, whether the person has lost their voice. Described herein are techniques for improving the diagnosis of health conditions by processing speech of a person from more than one time period.

Any appropriate health condition may be diagnosed using the techniques described herein. For example, the health conditions may include mental health conditions (e.g., stress, depression, anxiety, and post-traumatic stress disorder), concussions, Parkinson's disease, Alzheimer's disease, and congestive heart failure. In some implementations the health condition may include the likelihood of health-related events occurring, such as a likelihood that a patient will be rehospitalized after being released from a hospital (e.g., a likelihood of being rehospitalized after being treated for heart failure).

As used herein, time periods may be separated by any appropriate interval used by medical professionals when treating patients. In some circumstances, the time periods may be spaced months or years apart, but in some circumstances multiple time periods may be in the same day.

As used herein, speech includes any sounds emitted by the vocal tract of a person and these sounds need not include intelligible speech or sounds intended as spoken words. For example, speech may include sighs, breathy sounds, or grunts.

FIGS. 1A-D illustrate example architectures for processing speech with a mathematical model to diagnose a health condition. The mathematical models in FIGS. 1A-D may include any appropriate mathematical models, such as a neural network.

Figure 1A:
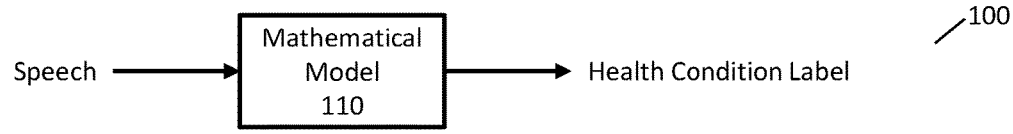
FIG. 1A is an example system for processing speech with a mathematical model to determine a health condition label.

FIG. 1A is an example system 100 for processing speech with mathematical model component 110 to determine a health condition label. The health condition label may include any appropriate label that is relevant to a medical diagnosis, such as a boolean value (indicating whether a person has a condition or not), a selection from a set of labels (e.g., "mild,", "medium," or "severe"), an integer value (e.g., on a scale of 1-10), or a floating point value (e.g., a temperature of 98.6 degrees).

Figure 1B:
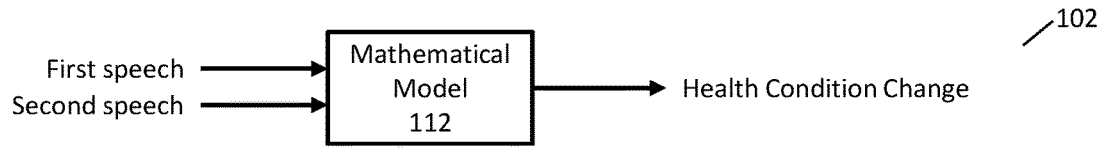
FIG. 1B is an example system for processing first speech from a first time period and second speech from a second time period with a mathematical model to determine a health condition change between the first time period and the second time period.

FIG. 1B is an example system 102 for processing first speech from a first time period and second speech from a second time period with mathematical model component 112 to determine a health condition change between the first time period and the second time period. The health condition change may be any appropriate value that may be used to indicate a change in a health condition, such as a boolean value (indicating a change or not), a selection from a set of labels (e.g., "better" or "worse"), an integer value, or a floating point value.

Figure 1C:
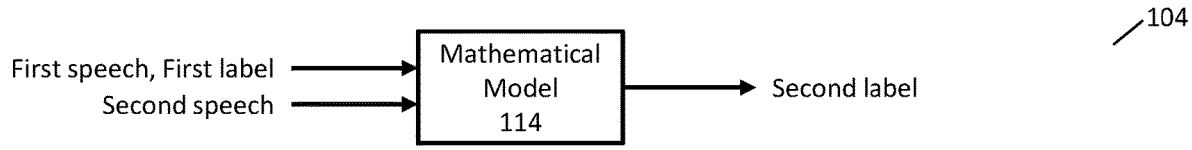
FIG. 1C is an example system for processing first speech from a first time period, a first health condition label from the first time period, and second speech from a second time period with a mathematical model to determine a second health condition label for the second time period.

FIG. 1C is an example system 104 for processing first speech from a first time period, a first health condition label from the first time period, and second speech from a second time period with mathematical model component 114 to determine a second health condition label for the second time period. The first health condition label may have been determined using any appropriate techniques, such as being determined by a person or a mathematical model. The first and second health condition labels may include any of the labels described herein.

Figure 1D:
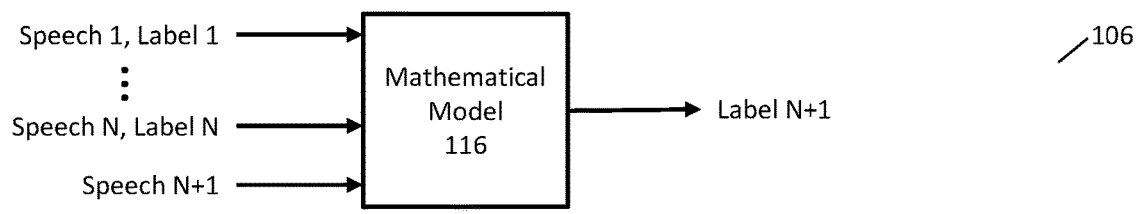
FIG. 1D is an example system for processing multiple previous pairs of speech and health condition labels from previous time periods and a current speech sample from a current time with a mathematical model to determine a health condition label for the current time.

FIG. 1D is an example system 106 for processing multiple previous pairs of speech and health condition labels from previous time periods and a current speech sample from a current time with mathematical model component 116 to determine a health condition label for the current time. The example of FIG. 1D indicates N previous pairs speech and health condition labels where N may be any number larger than one. The previous health condition labels may have been determined using any appropriate techniques, such as being determined by a person or a mathematical model. The previous and current health condition labels may include any of the labels described herein. The current time period may include any appropriate time period for which it is desired to compute a health condition label, and the processing of system 106 need not be performed at the time of receiving the current speech.

Additional details of implementations of FIGS. 1A-D are now described.

Figure 2:
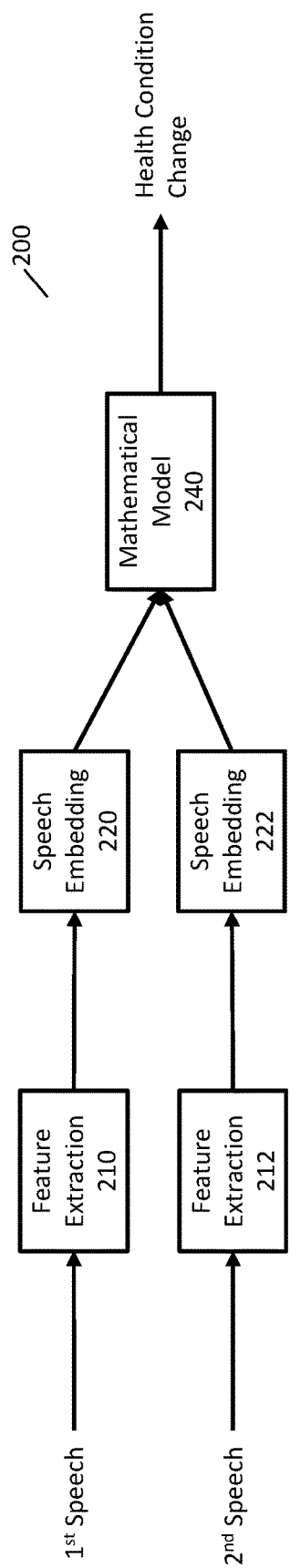
FIG. 2 is an example system for processing first speech from a first time period and second speech from a second time period with a mathematical model to determine a health condition change between the first time period and the second time period.

FIG. 2 is an example system 200 for processing first speech from a first time period and second speech from a second time period with a mathematical model to determine a health condition change between the first time period and the second time period.

In FIG. 2, first speech is processed by feature extraction component 210 to compute a first feature vector (or possibly a first sequence of feature vectors) and second speech is processed by feature extraction component 212 to compute a second feature vector (or possibly a second sequence of feature vectors). Feature extraction component 210 and feature extraction component 212 may compute the same types of features or may compute different types of features. The feature vectors may include any appropriate types of features, including but not limited to any of the features described in U.S. Pat. No. 10,152,988, which is incorporated herein by reference.

The features may include acoustic features, where acoustic features are any features computed from the speech data that do not involve or depend on performing speech recognition on the speech data (e.g., the acoustic features do not use information about the words spoken in the speech data). For example, acoustic features may include mel-frequency cepstral coefficients; perceptual linear prediction features; Wav2Vec features; prosodic features (such as pitch, energy, or probability of voicing); voice quality features (such as jitter, jitter of jitter, shimmer, or harmonics-to-noise ratio); or entropy.

The features may include language features where language features are computed using recognized text obtained via automatic speech recognition. For example, language features may include the words spoken in the speech; a speaking rate (e.g., the number of vowels or syllables per second); a number of pause fillers (e.g., "ums" and "ahs"); the difficulty of words (e.g., less common words); or the parts of speech of words following pause fillers. In some implementations, language features may include a determination of whether a person answered a question correctly. For example, a person may be asked what the current year is or who the President of the United States is. The person's speech may be processed to determine what the person said in response to the question and to determine if the person answered the question correctly.

In some implementations, feature extraction component 210 and feature extraction component 212 may perform speech recognition to obtain text corresponding to the speech and then output tokenized text as features, such as word-piece encodings, byte-pair encodings, or sentence-piece encodings. The tokenized text may be combined with any of the other features described herein.

A pair of mathematical models may then process the feature vectors. Speech embedding component 220 may process the first feature vector computed by feature extraction component 210 and compute a first speech embedding vector. Similarly, speech embedding component 222 may process the second feature vector computed by feature extraction component 212 and compute a second speech embedding vector.

As used herein, a speech embedding vector is a representation of the corresponding speech in a vector space where the position of the speech embedding vector in the vector space corresponds to information, qualities, or other aspects of the speech. For example, in some implementations, the position of the speech embedding vector may correspond to the meaning of the words in the speech so that speech embedding vectors for speech with similar meanings will be close to each other in the vector space (e.g., "Hello" and "Good morning").

Speech embedding component 220 and speech embedding component 220 may have the same architecture and parameters, may have the same architecture and different parameters, or may have different architecture and different parameters.

Speech embedding component 220 and speech embedding component 222 may be implemented using any appropriate techniques, such as a transformer neural network (such as a Bidirectional Encoder Representation from Transformer or BERT neural network), a fully-connected neural network (e.g., a multi-layer perceptron), a recurrent neural network, a convolutional neural network, or any combination of the foregoing neural networks. In some implementations, speech embedding component 220 and speech embedding component 222 may include one or more feed-forward neural network layers and one or more self-attention neural network layers.

Mathematical model component 240 processes the first speech embedding vector computed by speech embedding component 220 and the second speech embedding vector computed by speech embedding component 222 and computes a change value that indicates a change in a health condition, such as any of health condition change values described herein. In some implementations, mathematical model component 240 may concatenate the first speech embedding vector with the second speech embedding vector and process the concatenated vector with a mathematical model. Mathematical model component 240 may be implemented using any appropriate mathematical model, such as a linear model (e.g., matrix-vector multiplication or inner product) or a neural network (e.g., a fully-connected neural network; a feed-forward, fully-connected neural network; a multi-layer perceptron; a transformer neural network; a recurrent neural network; a convolutional neural network; or any of the other neural networks described herein).

In some implementations, mathematical model component 240 may be implemented using a transformer neural network, such as a BERT neural network. For example, the first and second speech encoding vectors may be concatenated to form an input vector for the transformer neural network. The change value may be an element of an output vector of the transformer neural network or the output of the transformer neural network may be followed by one or more layers (e.g., a linear layer) to compute the change value from the output of the transformer neural network.

In some implementations, mathematical model component 240 may be implemented using a recurrent neural network. For example, the first and second speech encoding vectors may be sequentially processed (in any appropriate order and optionally with separator tokens) by the recurrent neural network. The change value may be an element of an output vector of the recurrent neural network or the output of the recurrent neural network may be followed by one or more layers (e.g., a linear layer) to compute the change value from the output of the recurrent neural network.

Figure 3:
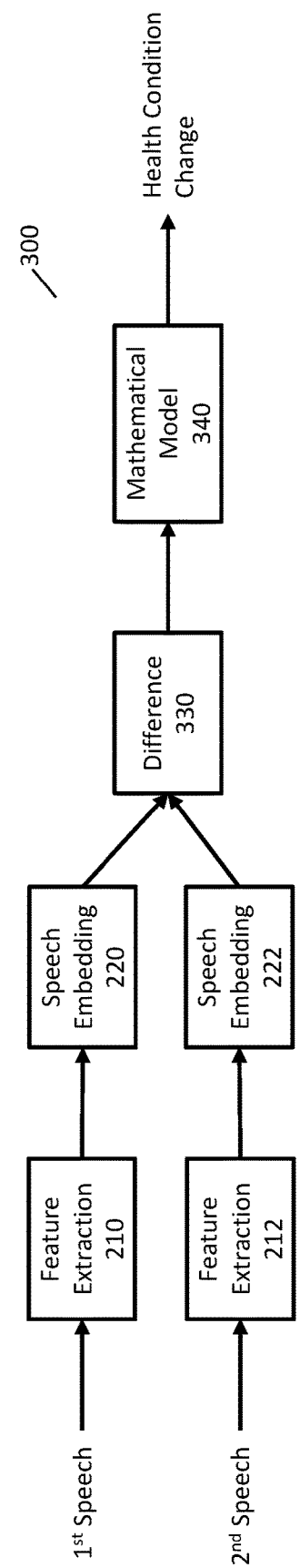
FIG. 3 is an example system for processing speech from two time periods with a mathematical model to determine a health condition change using an element-wise difference.

FIG. 3 is an example system 300 for processing speech from two time periods with a mathematical model to determine a health condition change value using an element-wise difference. In FIG. 3, feature extraction component 210, feature extraction component 212, speech embedding component 220, and speech embedding component 222 may be implemented as described above.

Difference component 330 receives the first speech embedding from speech embedding component 220 and the second speech embedding from speech embedding component 222 and computes a difference vector that is an element-wise difference of the two speech embedding vectors. For example, if a first element of the first speech embedding vector is "a" and the first element of the second speech embedding vector is "b", then the first element of the difference vector is "a-b".

Mathematical model component 340 processes the difference vector computed by difference component 330 and computes a change value that indicates a change in a health condition, such as any of health condition change values described herein. Mathematical model component 340 may be implemented using any appropriate techniques, such as any of the techniques described above for mathematical model component 240.

In some implementations, mathematical model component 340 may compute a health condition change value that is anti-symmetric given the inputs, meaning that if the speech inputs are swapped, then the output health condition change has the same magnitude but the opposite sign (e.g., the health condition change would switch from +3 to −3). For example, where mathematical model component 340 computes the health condition change by computing an inner product of the difference vector with a vector of parameters, the computation of the health condition change will be anti-symmetric.

Figure 4:
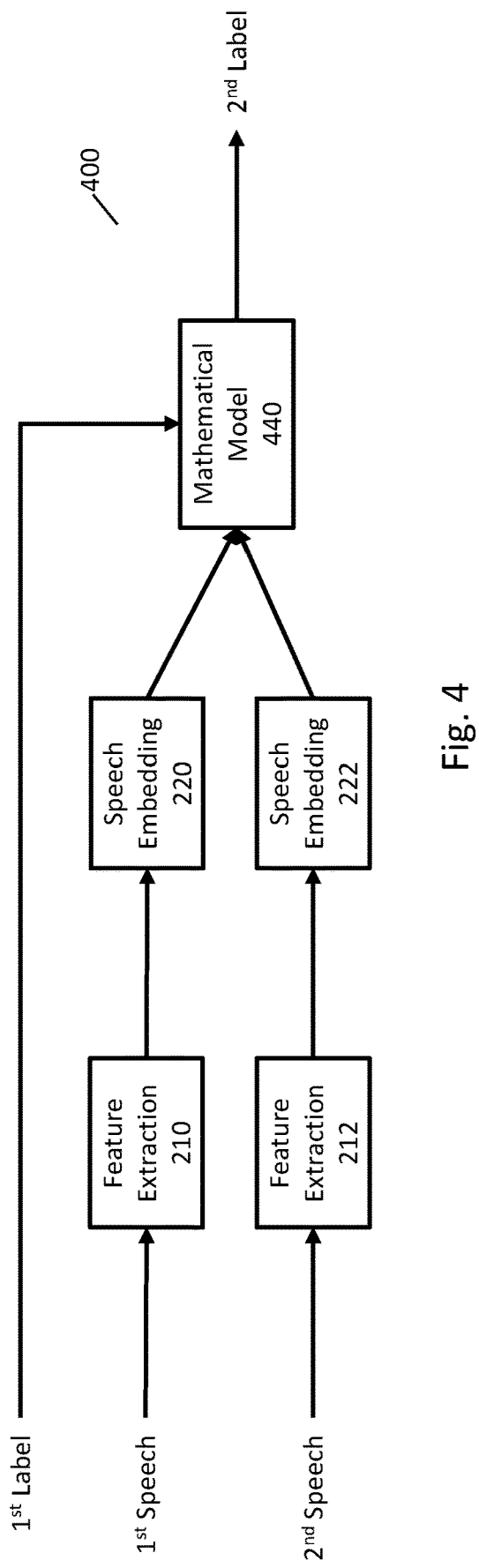
FIG. 4 is an example system for processing first speech and a first health condition label from a first time period and second speech from a second time period with a mathematical model to determine a second health condition label for the second time period.

FIG. 4 is an example system 400 for processing first speech and a first health condition label from a first time period and second speech from a second time period with a mathematical model to determine a second health condition label for the second time period. The first and second health condition labels may include any appropriate labels, such as any of the labels described herein.

In FIG. 4, feature extraction component 210, feature extraction component 212, speech embedding component 220, and speech embedding component 222 may be implemented as described above.

Mathematical model component 440 processes the first speech embedding vector computed by speech embedding component 220, the second speech embedding vector computed by speech embedding component 222, and the first health condition label corresponding to the first time period and computes a second health condition label corresponding to the second time period. The first health condition label may be combined with the first and second speech embedding vectors using any appropriate techniques, such as concatenation (e.g., with a transformer neural network) or sequential processing (e.g., with a recurrent neural network). Mathematical model component 440 may be implemented using any appropriate techniques, such as any of the techniques described above for mathematical model component 240.

In some implementations, mathematical model component 440 may implement regression techniques, such as any combination of linear regression, non-linear regression, multiple regression, multivariate regression, semiparametric regression, or nonparametric regression (e.g., using nearest neighbors, regression trees, kernel regression, local regression, multivariate adaptive regression splines, neural networks, support vector regression, or smoothing splines).

In some implementations, mathematical model component 440 may compute a difference vector as an element-wise difference between the first speech embedding and the second speech embedding and then use the difference vector to compute a value that indicates a change in a health condition between the first time period and the second time period. Mathematical model component 440 may then use the first label and the value that indicates a change in the health condition to compute the second health condition label for the second time period. For example, the second health condition label may be computed by adding the first health condition label and the change.

Figure 5:
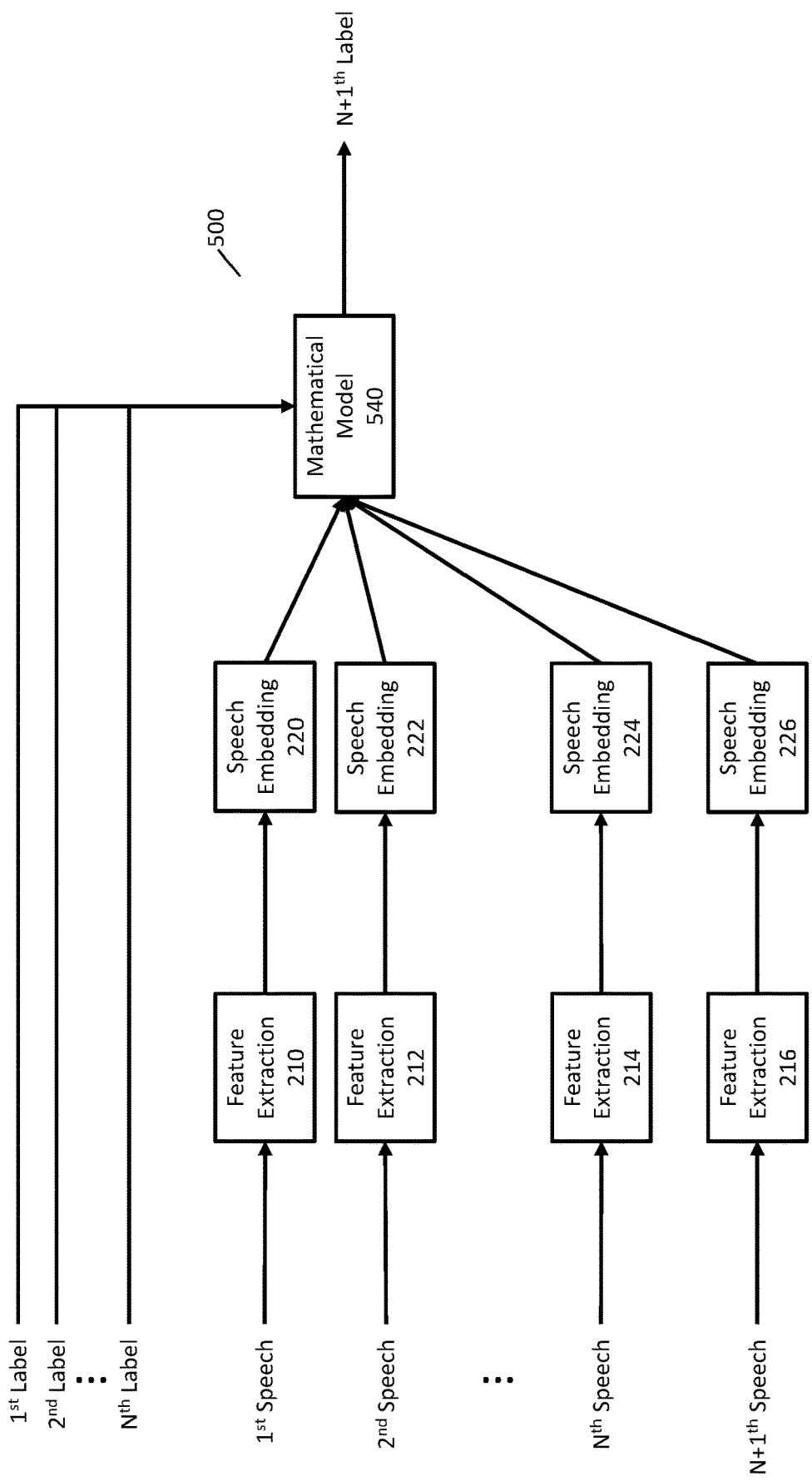
FIG. 5 is an example system for processing multiple pairs of previous speech and health condition labels from previous time periods and current speech from a current time period with a mathematical model to determine a current health condition label for the current time period.

FIG. 5 is an example system 500 for processing multiple pairs of previous speech and health condition labels from previous time periods and current speech from a current time period with a mathematical model to determine a current health condition label for the current time period. The health condition labels may include any appropriate labels, such as any of the labels described herein.

In FIG. 5, N speech inputs and N labels are shown where N corresponds to any number larger than one. The N speech inputs and labels may be obtained from medical records of a patient and may correspond to previous visits of the patient at different time periods.

The N+1st speech input may be a speech input for which it is desired to compute a health condition label, and the N+1st speech input may correspond to a most recent visit of a patient or a current time. System 500 processes the N pairs of speech inputs and labels and the N+1st speech input to compute the N+1st health condition label.

In FIG. 5, feature extraction component 210, feature extraction component 212, feature extraction component 214, and feature extraction component 216 may be implemented using any of the feature extraction techniques described herein. Each instance of feature extraction component may compute the same types of features or different types of features.

Speech embedding component 220, speech embedding component 222, speech embedding component 224, and speech embedding component 226 may compute a speech embedding vector from a feature vector using any of the techniques described herein. Each instance of speech embedding component may use the same or different neural network architectures and parameters.

Mathematical model component 540 processes the N labels and the N+1 speech embedding vectors to compute the N+1 st health condition label for the N+1 st speech input. Mathematical model component 540 may be implemented using any appropriate techniques. For example, mathematical model component 540 may be implemented using any of the techniques described above for mathematical model component 240 or mathematical model component 440 where those techniques are adapted for additional input values using techniques known to one of skill in the art.

Figure 6:
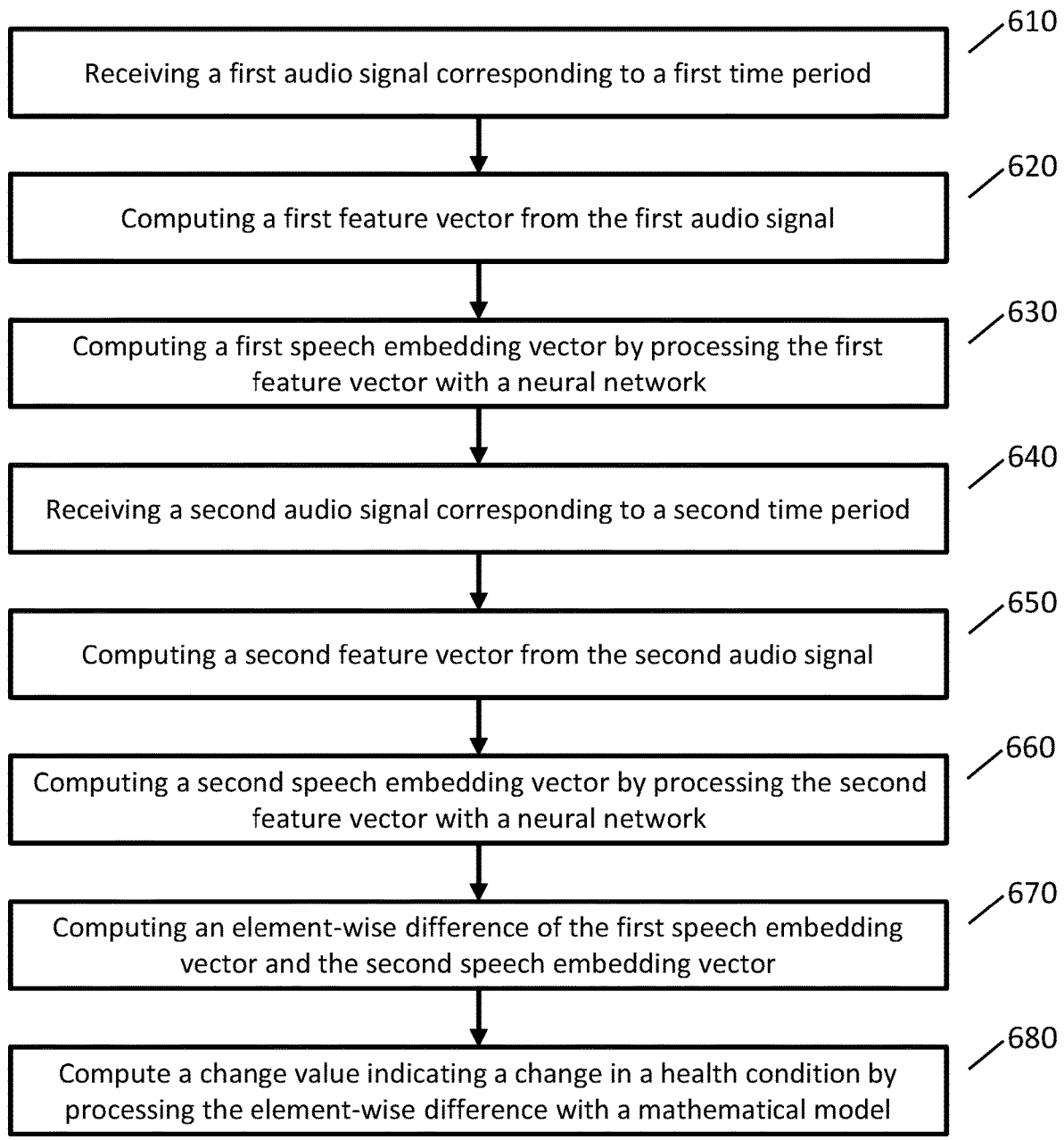
FIG. 6 is a flowchart of an example method for processing speech from two time periods with a mathematical model to determine a health condition change using an element-wise difference.

FIG. 6 is a flowchart of an example method for processing speech from two time periods with a mathematical model to determine a health condition change using an element-wise difference.

At step 610, a first audio signal is received corresponding to a first time period, where the first audio signal comprises speech of a first person. The first audio signal may be received using any appropriate techniques, such as via an API call or retrieved from storage.

At step 620, a first feature vector is computed from the first audio signal. The first feature vector may include any appropriate features, such as any of the features described herein. In some implementations, the features may include word-piece encodings corresponding to text of speech in the audio signal determined using automatic speech recognition. In some implementations, the features may include acoustic features.

At step 630, a first speech embedding vector is computed by processing the first feature vector with a neural network. The neural network may be any appropriate neural network, such as any of the neural networks described herein. In some implementations, the neural network may include a transformer neural network. In some implementations, the neural network may include one or more feed-forward neural network layers and one or more self-attention neural network layers.

At step 640, a second audio signal is received corresponding to a second time period, wherein the second audio signal comprises speech of the first person. The second audio signal may be received as described above for step 610.

At step 650, a second feature vector is computed from the second audio signal. The second feature vector may be computed as described above for step 620.

At step 660, a second speech embedding vector is computed by processing the second feature vector with the neural network (or possibly a different neural network). The second speech embedding may be computed as described above for step 630.

At step 670, an element-wise difference vector is computed between the first speech embedding vector and the second speech embedding vector. The element-wise difference vector may be computed using any of the techniques described herein.

At step 680, a change value indicating a change in a health condition is computed by processing the element-wise difference vector with a mathematical model. The change value may indicate a change in the health condition between the first time period and the second time period. The mathematical model may be any appropriate mathematical model, such as any of the mathematical models described herein. In some implementations, the change value may be an anti-symmetric change value. In some implementations, the mathematical model may process the element-wise difference vector with any combination of an inner product, a matrix-vector multiplication, or a neural network.

In some implementations, some of steps 610-630 may be performed in advance and the first feature vector or the first speech embedding may be stored for later use. For example, some of steps 610-630 may be performed soon after a first medical visit where the first audio sample is obtained. The first feature vector or the first speech embedding may be stored so that they may be used the next time the person is receiving medical care. Steps 640-680 may be performed after a subsequent medical visit, which may be days, weeks, months, or years after the first medical visit.

In some implementations, the steps of FIG. 6 may be performed for multiple previous medical visits to compute multiple change values. For example, a third audio signal may have been obtained from another previous medical visit. A second change value may be computed using the third audio signal, a third feature vector, a third speech embedding vector, and a second element-wise difference vector computed using the second speech embedding vector and the third speech embedding vector.

In some implementations, a first health condition label may be obtained corresponding to the first time period. The first health condition label may have been determined using any appropriate techniques, such as any of the techniques described herein. A second health condition label for the second time period may then be computed using the first health condition label and the change value. The second health condition label may be computed using any appropriate techniques, such as by adding the first health condition label and the change value.

Figure 7:
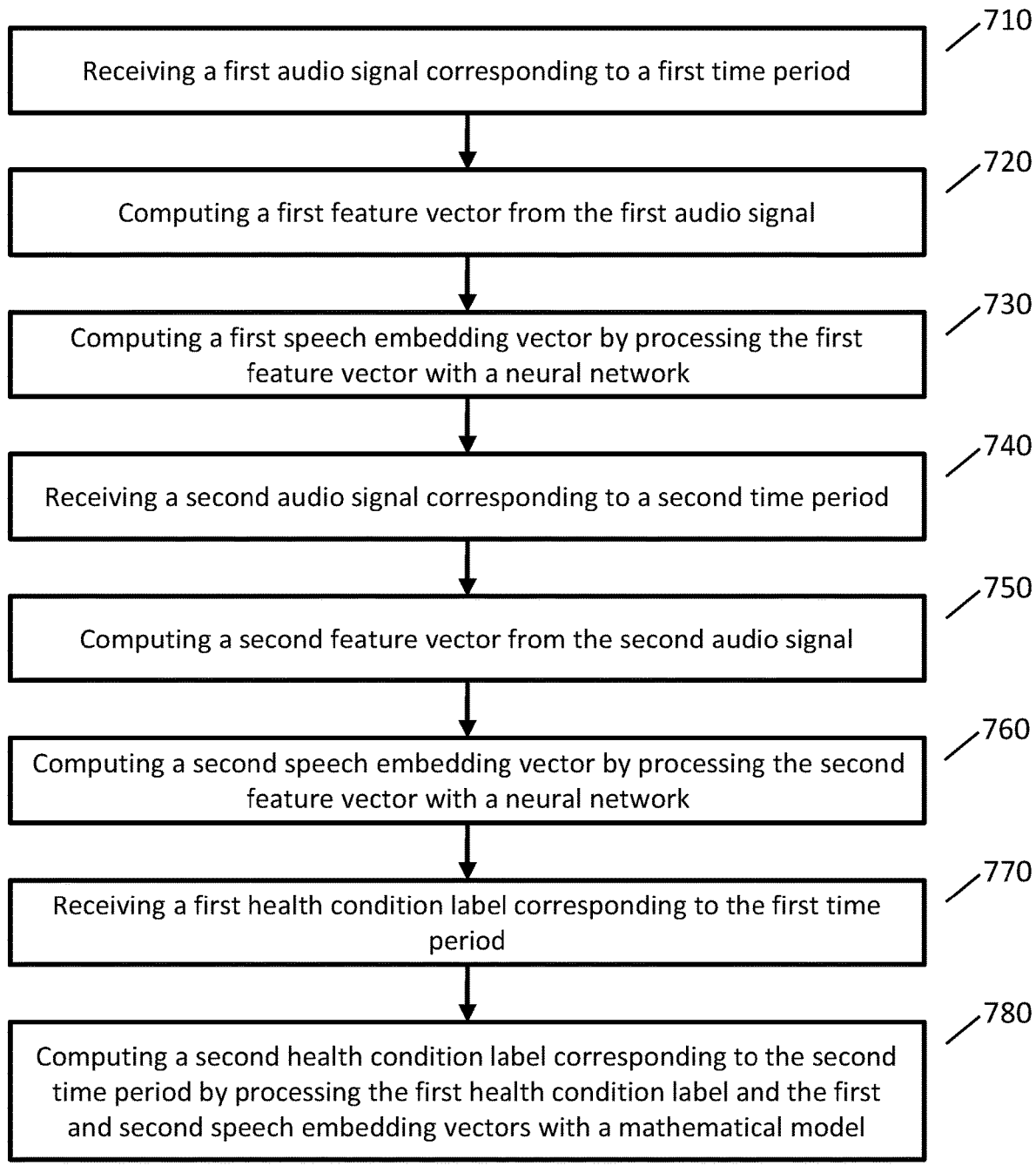
FIG. 7 is a flowchart of an example method for processing first speech and a first health condition label from a first time period and second speech from a second time period with a mathematical model to determine a second health condition label for the second time period.

FIG. 7 is a flowchart of an example method for processing first speech and a first health condition label from a first time period and second speech from a second time period with a mathematical model to determine a second health condition label for the second time period.

In FIG. 7, steps 710-760 may be implemented as described above for steps 610-660 of FIG. 6.

At step 770, a first health condition label corresponding to the first time period is obtained. The first health condition label may be any of the health condition labels described herein and may be obtained using any appropriate techniques. For example, the first health condition label may be stored with the first audio signal (or the first feature vector or first speech embedding vector).

At step 780, a second health condition label corresponding to the second time period is computed by processing the first health condition label and the first and second speech embedding vectors with a mathematical model. The mathematical model may be any appropriate mathematical model, such as a neural network. In some implementations, the mathematical model may compute the second health condition label using linear or nonlinear regression techniques.

For any of the techniques described herein, the parameters of the mathematical models (including neural networks) may be learned or trained using a training process. Any appropriate training process may be used, such as supervised training or unsupervised training. The training process may include a training corpus of audio files and the training corpus may also include training labels that indicate health condition labels corresponding to audio files or change values corresponding to pairs of audio files. The parameters of the mathematical models may be learned through an iterative training process. For example, the training process may include a forward pass that processes the training data to compute predictions (e.g., health condition labels or change values), error values may be computed using the predictions and the training labels, and a backward pass may be performed to update the mathematical model parameters using the error values (e.g., using stochastic gradient descent). The training process may continue until a desired convergence criterion has been obtained.

Figure 8:
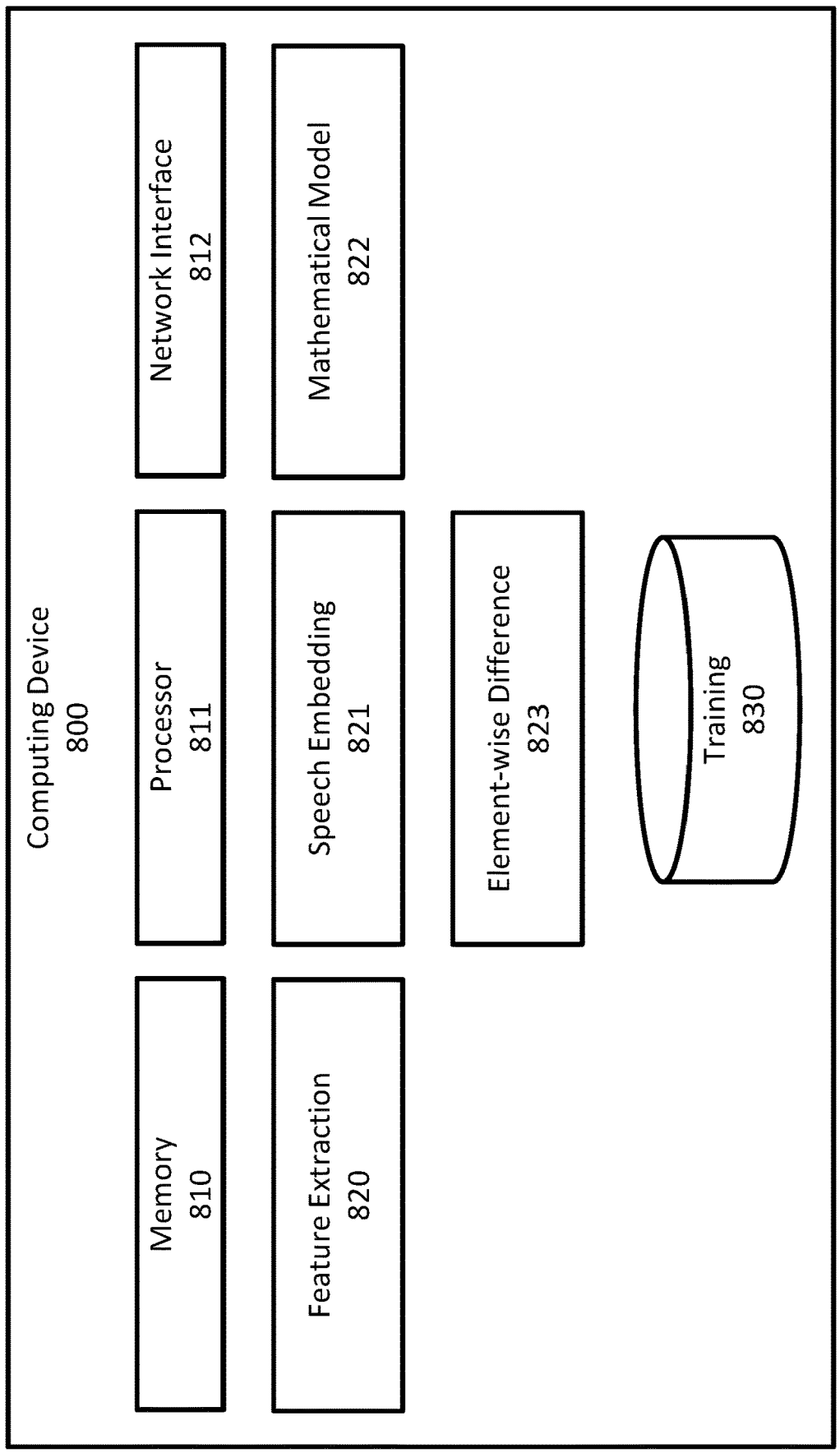
FIG. 8 illustrates components of one implementation of a computing device for implementing any of the techniques described herein.

FIG. 8 illustrates components of one implementation of a computing device 800 for implementing any of the techniques described herein. In FIG. 8, the components are shown as being on a single computing device, but the components may be distributed among multiple computing devices, such as a system of computing devices, including, for example, an end-user computing device (e.g., a smart phone or a tablet) and/or a server computer (e.g., cloud computing).

Computing device 800 may include any components typical of a computing device, such as volatile or nonvolatile memory 810, one or more processors 811, and one or more network interfaces 812. Computing device 800 may also include any input and output components, such as displays, keyboards, and touch screens. Computing device 800 may also include a variety of components or modules providing specific functionality, and these components or modules may be implemented in software, hardware, or a combination thereof. Computing device 800 may include one or more non-transitory, computer-readable media comprising computer-executable instructions that, when executed, cause a processor to perform actions corresponding to any of the techniques described herein. Below, several examples of components are described for one example implementation, and other implementations may include additional components or exclude some of the components described below.

Computing device 800 may have a feature extraction component 820 that may compute feature vectors from an audio signal using any of the techniques described herein. Computing device 800 may have a speech embedding component 821 that may compute a compute a speech embedding vector from a feature vector using any of the techniques described herein. Computing device 800 may have a mathematical model component 822 that may compute a health condition label or a health condition change value using any of the techniques described herein. Computing device 800 may have an element-wise difference component 823 that may compute an element-wise difference of two vectors using any of the techniques described herein.

Computing device 800 may include or have access to various data stores. Data stores may use any known storage technology such as files, relational databases, non-relational databases, or any non-transitory computer-readable media. Computing device 800 may have a training data store 830 that stores training data that may be used to train any of the mathematical models described herein.

The methods and systems described herein may be deployed in part or in whole through a machine that executes computer software, program codes, and/or instructions on a processor. "Processor" as used herein is meant to include at least one processor and unless context clearly indicates otherwise, the plural and the singular should be understood to be interchangeable. Any aspects of the present disclosure may be implemented as a computer-implemented method on the machine, as a system or apparatus as part of or in relation to the machine, or as a computer program product embodied in a computer readable medium executing on one or more of the machines. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference in the entirety.

What is claimed is:

1. A computer-implemented method, comprising:
    training a neural network using a training corpus of audio files and training labels that indicate health condition labels corresponding to the audio files, change values corresponding to pairs of audio files, or a combination thereof;
    receiving a first audio signal corresponding to a first time period, wherein the first audio signal comprises speech of a person;
    computing a first feature vector from the first audio signal;
    computing a first speech embedding vector by processing the first feature vector with the neural network;
    obtaining a first health condition label indicating a health condition at the first time period;
    combining the first health condition label with the first speech embedding vector using the neural network;
    receiving a second audio signal corresponding to a second time period, wherein the second audio signal comprises a second speech of the person;
    computing a second feature vector from the second audio signal;
    computing a second speech embedding vector by processing the second feature vector with the neural network;
    computing a difference vector comprising an element-wise difference between each element of the first speech embedding vector and each element of the second speech embedding vector;
    computing a change value indicating a change in the health condition between the first time period and the second time period by processing the difference vector with a mathematical model; and
    computing a second health condition label indicating the health condition at the second time period as a function of the first health condition label and the change value using the mathematical model.

2. The computer-implemented method of claim 1, wherein computing the second health condition label comprises adding the first health condition label and the change value.

3. The computer-implemented method of claim 1, wherein:
    computing the first feature vector comprises (i) performing speech recognition on the first audio signal to obtain recognized text and (ii) obtaining word-piece encodings corresponding to the recognized text; and
    the neural network comprises a plurality of feed-forward neural network layers and a plurality of self-attention neural network layers.

4. The computer-implemented method of claim 1, wherein the mathematical model comprises a second neural network.

5. The computer-implemented method of claim 1, wherein the mathematical model comprises a fully-connected neural network.

6. The computer-implemented method of claim 1, wherein the health condition corresponds to stress, depression, anxiety, post-traumatic stress disorder, concussion, Parkinson's disease, Alzheimer's disease, or congestive heart failure.

7. The computer-implemented method of claim 1, wherein computing the change value comprises computing an anti-symmetric change value.

8. A system, comprising at least one computer configured to:
- train a neural network using a training corpus of audio files and training labels that indicate health condition labels corresponding to the audio files, change values corresponding to pairs of audio files, or a combination thereof;
- receive a first audio signal corresponding to a first time period, wherein the first audio signal comprises speech of a person;
- compute a first feature vector from the first audio signal;
- compute a first speech embedding vector by processing the first feature vector with the neural network;
- obtain a first health condition label indicating a health condition at the first time period;
- combine the first health condition label with the first speech embedding vector using the neural network;
- receive a second audio signal corresponding to a second time period, wherein the second audio signal comprises a second speech of the person;
- compute a second feature vector from the second audio signal;
- compute a second speech embedding vector by processing the second feature vector with the neural network;
- compute a difference vector comprising an element-wise difference between each element of the first speech embedding vector and each element of the second speech embedding vector;
- compute a change value indicating a change in the health condition between the first time period and the second time period by processing the difference vector with a mathematical model; and
- compute a second health condition label indicating the health condition at the second time period as a function of the first health condition label and the change value using the mathematical model.

9. The system of claim 8, wherein the first feature vector includes acoustic features.

10. The system of claim 8, wherein the neural network comprises a transformer neural network.

11. The system of claim 8, wherein the mathematical model comprises a fully-connected neural network.

12. The system of claim 8, wherein the at least one computer is configured to:
- receive a third audio signal corresponding to a third time period, wherein the third audio signal comprises a third speech of the person;
- compute a third feature vector from the third audio signal;
- compute a third speech embedding vector by processing the third feature vector with the neural network;
- compute a second element-wise difference between the third speech embedding vector and the second speech embedding vector; and
- compute a second change value indicating a change in the health condition between the third time period and the second time period by processing the second element-wise difference with the mathematical model.

13. The system of claim 8, wherein the at least one computer is configured to compute the change value by computing an anti-symmetric change value.

14. The system of claim 8, wherein the at least one computer is configured to compute the first feature vector by (i) performing speech recognition on the first audio signal to obtain recognized text and (ii) obtaining word-piece encodings corresponding to the recognized text.

15. One or more non-transitory computer-readable media comprising computer-executable instructions that, when executed, cause at least one processor to perform actions comprising:
- training a neural network using a training corpus of audio files and training labels that indicate health condition labels corresponding to the audio files, change values corresponding to pairs of audio files, or a combination thereof;
- receiving a first audio signal corresponding to a first time period, wherein the first audio signal comprises speech of a person;
- computing a first feature vector from the first audio signal;
- computing a first speech embedding vector by processing the first feature vector with the neural network;
- obtaining a first health condition label indicating a health condition at the first time period;
- combining the first health condition label with the first speech embedding vector using the neural network;
- receiving a second audio signal corresponding to a second time period, wherein the second audio signal comprises a second speech of the person;
- computing a second feature vector from the second audio signal;
- computing a second speech embedding vector by processing the second feature vector with the neural network;
- computing a difference vector comprising an element-wise difference between each element of the first speech embedding vector and each element of the second speech embedding vector;
- computing a change value indicating a change in the health condition between the first time period and the second time period by processing the difference vector with a mathematical model; and
- computing a second health condition label indicating the health condition at the second time period as a function of the first health condition label and the change value using the mathematical model.

16. The one or more non-transitory computer-readable media of claim 15, wherein the mathematical model comprises a fully-connected neural network.

17. The one or more non-transitory computer-readable media of claim 15, wherein computing the change value comprises computing an anti-symmetric change value.

18. The one or more non-transitory computer-readable media of claim 15, wherein the first feature vector includes acoustic features.

19. The one or more non-transitory computer-readable media of claim 15, wherein computing the first feature vector comprises (i) performing speech recognition on the first audio signal to obtain recognized text and (ii) obtaining word-piece encodings corresponding to the recognized text.

* * * * *